United States Patent
Somerville et al.

(10) Patent No.: US 8,980,227 B2
(45) Date of Patent: *Mar. 17, 2015

(54) DERMAL REJUVENATION COMPOSITIONS AND METHODS

(75) Inventors: Kate Somerville, West Hollywood, CA (US); Fred Khoury, Chatsworth, CA (US)

(73) Assignee: Kate Somerville Skincare, LLC, Beverly Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/587,545

(22) Filed: Aug. 16, 2012

(65) Prior Publication Data

US 2013/0045290 A1    Feb. 21, 2013

Related U.S. Application Data

(60) Provisional application No. 61/524,021, filed on Aug. 16, 2011.

(51) Int. Cl.
*A61K 31/726*    (2006.01)
*A61K 9/12*    (2006.01)
*A61K 36/185*    (2006.01)

(52) U.S. Cl.
CPC ............... *A61K 9/12* (2013.01); *A61K 31/726* (2013.01); *A61K 36/185* (2013.01)
USPC ............... 424/45; 424/47; 424/774; 424/778; 424/779; 514/42

(58) Field of Classification Search
USPC .................................. 424/400; 514/937, 938
See application file for complete search history.

(56) References Cited

U.S. PATENT DOCUMENTS

| | | | |
|---|---|---|---|
| 5,637,318 | A | 6/1997 | Gross et al. |
| 5,733,572 | A | 3/1998 | Unger et al. |
| 5,738,859 | A | 4/1998 | Posner |
| 5,840,309 | A | 11/1998 | Herstein et al. |
| 5,972,360 | A | 10/1999 | Braun |
| 6,440,429 | B1 | 8/2002 | Torizuka et al. |
| 6,649,145 | B2 | 11/2003 | McGrath et al. |
| 7,357,937 | B2 | 4/2008 | Hsu et al. |
| 2002/0034489 | A1 | 3/2002 | Wiegland et al. |
| 2003/0103922 | A1 | 6/2003 | Garrison et al. |
| 2005/0143324 | A1* | 6/2005 | Mastrodonato et al. ........ 514/27 |
| 2008/0003271 | A1* | 1/2008 | Abdellaoui et al. .......... 424/445 |
| 2010/0144861 | A1 | 6/2010 | Huvard et al. |
| 2011/0044920 | A1 | 2/2011 | Hines et al. |

FOREIGN PATENT DOCUMENTS

| | | |
|---|---|---|
| DE | 25 34 315 A1 | 2/1976 |
| EP | 0358528 A2 | 3/1990 |
| EP | 1549281 B1 | 1/2007 |
| JP | 62-093211 | 4/1987 |
| KR | 2008-0026924 A | 3/2008 |
| WO | WO-2009-102487 A2 | 8/2009 |

OTHER PUBLICATIONS

Fiflow® BTX (2004, http://barikisoken.com/fiflow2.pdf).*
Fiflow cream (Jun. 2011, http://www.kemcare.com/pdf.php?file_name=135202004+-+Skin+Creams+%26+Lotions+-+Face+-+With+Fiflow+BTX.pdf).*
Hyacare® 50 (2008, http://www.finecon.sk/admin/pdf/DS_HyaCare_50_e.pdf).*
Butnariu et al. \African J. of Biotech, Jun. 29, 2011, vol. 10, 5900-5909.*
Evonik Industries, "HyaCare® 50," 2010, 5 pages.
Evonik Industries, "Press Release: HyaCare® Filler CL—the topical wrinkle smoother," May 18, 2010, Retrieved from: http://corporate.evonik.com/en/media/archive/Pages/news-details.aspx?newsid=12057.
KemCare Speciality Chemicals, "Advanced® BTX: Liquid Surgery Without Scars, A successful fight against time," 2010, 10 pages.
KemCare Speciality Chemicals, "Fiflow BTX," 2010, Retrieved from: http://www.kemcare.com/products/fiflow-btx.
International Search Report dated Feb. 20, 2013, issued in PCT/US2012/051158.
INCI (http://www.specialchem4cosmetics.com/services/inci/index.aspx for ethanol, isododecane, glycereth-26, polysorbate 20, polydecene, phenoxyethanol and sodium lauroyl glutamate), 2009.
OXYGESKIN, Silab, 3 pages, Oct. 2010.
INCI Directory, Tropaeolum Majus Flower/Leaf/Stem Extract, 2014 SpecialChem, Jul. 8, 2009.
INCI Directory, Acrylates/C10-30 Alkyl Acrylate Crosspolymer, 2014 SpecialChem, Feb. 18, 2009.
Aeropres Incorporated, Material Safety Data Sheet, pp. 1-6, Jun. 1, 2008.
Haranges, SoliancE Naturally Innovative, 2 pages, Nov. 2012.
SoliancE Naturally Innovative, Cristalhyal/Vitalhyal, The Moisturizing Reference, 9 pages, Feb. 2012.
INCI (http://www.specialchem4cosmetics.com/services/inci/index.aspx for ethanol, isododecane, glycereth-26, polysorbate 20, polydecene, phenoxyethanol and sodium lauroyl glutamate).
Intraceutical Atoxelene ("Intraceutical", 2009, http://www.groomed-la.com/2009/12/product-obession-intraceuticals-atoxelene-line-wand.html.

(Continued)

*Primary Examiner* — Brian-Yong Kwon
*Assistant Examiner* — Kauser M Akhoon
(74) *Attorney, Agent, or Firm* — Venable LLP; Michele V. Frank, Esq.

(57) ABSTRACT

The present invention relates, e.g., to a system for treating damaged skin, comprising a cosmeceutical formulation comprising about 1-10% of a mixture of perfluorocarbons (PFC's) of at least three different molecular weights, and about 0.001-5% hyaluronic acid (HA) of molecular weight about 100 kDa or less, packaged in an aerosol spray container.

25 Claims, 3 Drawing Sheets

(56) References Cited

OTHER PUBLICATIONS

Oxygeskin, Silab, 3 pages.
INCI Directory, Tropaeolum Majus Flower/Leaf/Stem Extract, 2014 SpecialChem.
INCI Directory, Acrylates/C10-30 Alkyl Acrylate Crosspolymer, 2014 SpecialChem.
Aeropres Incorporated, Material Safety Data Sheet, pp. 1-6.
Haranges, SoliancE Naturally Innovative, 2 pages.
Jiangsu High Hope Int'l Group Sunshine Chemical Corporation, MoisCFL®Ha Sodium Hyaluronate Application, www.cflchem.com, 6 pages, Dec. 7, 2011.
SoliancE Naturally Innovative, Cristalhyal/Vitalhyal, The Moisturizing Reference, 9 pages.
Jiangsu High Hope Int'l Group Sunshine Chemical Corporation, Skin Lightening Lotion(O/W), www.cflchem.com, Dec. 7, 2011.
Jiangsu High Hope Int'l Group Sunshine Chemical Corporation, Antiwrinkle & Antiaging Cream (O/W), www.cflchem.com, Dec. 7, 2011.
European Application No. 12 82 3411: Search Report mailed Jan. 15, 2015.
Database GNPD, Mintel: "Liquid Lift Advanced Wrinkle Treatment", www.gnpd.com, May 2012.

* cited by examiner

DERMAL REJUVENATION COMPOSITIONS AND METHODS

This application claims the benefit of the filing date of U.S. provisional application 61/524,021, filed Aug. 16, 2011, which is incorporated by reference herein in its entirety.

FIELD OF THE INVENTION

This invention relates to cosmeceutical compositions and methods, e.g. a formulation comprising low molecular weight hyaluronic acid and perfluorocarbons of various molecular weights, packaged into a hand-held aerosol/propellant device; and a method of using it to treat damaged skin.

BACKGROUND INFORMATION

Currently, methods for treating damaged, such as aging, skin require visits to a facility, such as a clinic. For example, hyperbaric pressurized oxygen machines can be used to deliver oxygen to the skin. However, such methods are inconvenient, and require trained personnel and pressurized oxygen tanks, which must be sterilized and maintained. Other treatment methods involve painful, invasive and expensive injections, which must also be administered by trained personnel.

There is a need for a simple, effective method of skin treatment that can be administered in a home setting.

DESCRIPTION OF EMBODIMENTS OF THE INVENTION

Figure 1:
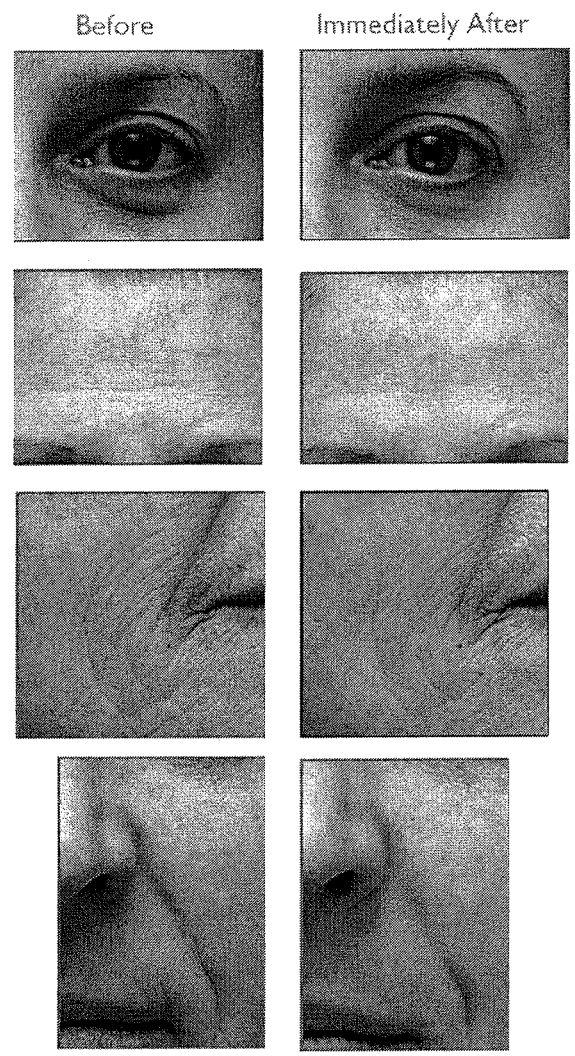
FIG. 1 shows pictures before and after treatment with a system of the invention.

The present inventors have found, surprisingly, that a combination of a perfluorocarbon (PFC) mixture comprising different molecular weight PFC's and low molecular weight hyaluronic acid, when delivered by an aerosol/propellant hand-held device, results in dermal rejuvenation, including significant effects on damaged skin, such as hydration benefits, skin plumping and line and wrinkle reduction. By packaging the formulation under pressure in a sealed container, to be delivered as an aerosol, the instability (evaporation, dispersion) of volatile components such as PFC's is reduced significantly, resulting in greatly increased stability compared to, for example, serums, creams, or other formulations comprising these ingredients but stored in and dispensed by, e.g., hand pumps. In the presently claimed systems in which the formulations are stored under pressure in closed containers and are dispensed as aerosols, the formulations remain in an active form (e.g., the PFC's retain the ability to entrap oxygen which can be delivered to the skin) for at least one year and often for 2, 3 4 or more years. This stability of the activity is an important advantage of this embodiment of the present invention.

The formulations are cosmeceutical, i.e. suitable for topical administration to a subject, with cosmetically and/or pharmaceutically acceptable carriers and components, and providing cosmetic and/or pharmaceutical effects. One aspect of the invention is a system for treating damaged skin, comprising a cosmeceutical formulation comprising a. a mixture of perfluorocarbons (PFC's) of at least three different molecular weights (e.g., selected from perfluoropropane, perfluorobutane, perfluoropentane, perfluorohexane, perfluorodecalin, perfluorodimethyl-cyclohexane, perfluoroperhydrophenanthrene, pentafluoro-propane, perfluorotripropylamine, $C_6$-$C_9$ perfluoroalkanes, perfluoroperhydrofluoranthrene, perfluorodecalin, perfluoroperhydro-phenanthrene, bis(perfluor-hexyl)-1,2-ethene, perfluoro-1,3-dimethylcyclohexane, perfluoro-methyldecalin, perfluoroisopropyldecalin, a mixture of perfluorodixylylmethane and perfluorodixylylethane, and/or a mixture of perfluoroperhydrophenanthrene and perfluoro n-butyl decalin), and b. hyaluronic acid (HA) of molecular weight about 100 kDa or less (e.g., about 50 kDa or less, or about 50 kDa), packaged in an aerosol spray, hand-held container (e.g. stored under pressure, with a propellant, and administered in the form of an aerosol).

In one embodiment of the invention, the cosmeceutical formulation is an aqueous formulation. In another embodiment, the cosmeceutical formulation comprises an oil and water emulsion (e.g., comprising about 80% purified water and about 10% components of an oil phase).

By "purified water" is meant water that does not contain ingredients which would be harmful to, or would cause adverse reactions to, the skin of a subject, such as a human. Distilled water and/or deonized water can be used.

In embodiments of the invention, the concentration of the mixture of perfluorocarbons can be up to, about, or not more than 1%, 5%, 6%, 7%, 8%, 9%, 10%, 11%, 12%, 13%, 14%, 15%, 16%, 18%, 20%, or 25%

In embodiments of the invention, the HA can be in a range of about 0.0001 to 5%, e.g., up to, about, or greater than about 0.0001%, 0.0005%, 0.001%, 0.005%, 0.01%, 0.02%, 0.04%, 0.06%, 0.08%, 0.10%, 0.12%, 0.14%, 0.16%, 0.18%, 0.2%, 0.5%, 1%, 3% or 5%.

The formulation may contain, for example 1% PFC's and 0.01% HA, 20% PFC's and 3% HA, 1% PFC's and 3% HA, 20% PFC's and 0.01% HA, 5% PFC's and 0.05% HA, 10% PFC's and 0.1% HA, 10% PFC's and 1% HA, or 5% PFC's and 1% HA.

Another aspect of the invention is a method for treating damaged skin, comprising administering with an aerosol spray hand-held container a cosmeceutical formulation comprising a. a mixture of perfluorocarbons (PFC's) of at least three different molecular weights (e.g., selected from perfluoropropane, perfluorobutane, perfluoropentane, perfluorohexane, perfluorodecalin, perfluorodimethylcyclohexane, perfluoroperhydrophenanthrene, pentafluoropropane, perfluorotripropylamine, $C_6$-$C_9$ perfluoroalkanes, perfluoroperhydrofluoranthrene, perfluorodecalin, perfluoroperhydrophenanthrene, bis(perfluor-hexyl)-1,2-ethene, perfluoro-1,3-dimethylcyclohexane, perfluoromethyldecalin, perfluoroisopropyldecalin, a mixture of perfluorodixylylmethane and perfluorodixylylethane, and a mixture of perfluoroperhydrophenanthrene and perfluoro n-butyl decalin), and b. hyaluronic acid (HA) of molecular weight about 100 kDa or less (e.g., about 50 kDa or less, or about 50 kDa).

In one embodiment of this method, the cosmeceutical formulation is an aqueous formulation. In another embodiment, the cosmeceutical formulation comprises an oil and water emulsion (e.g., comprising about 60%, 70%, 80%, or 90% purified water and about 5%, 10%, 20%, or 35% components of an oil phase, or other values).

In addition to the components noted above, a cosmeceutical formulation of the invention can comprise one or more additional components. These include, e.g., niacin or other vitamins, minerals, amino acids, antioxidants, blood dilating ingredients, and natural enjoyable fragrances. For example, additional components can include one or more of: HSC (Hydrophobic Sphingolipid Complex), Atoxelene (which comprises the stabilized retinal, Retistar™); a light, natural fragrance, such as rose floral water, vanilla floral water, or prickly pear.

In one embodiment of the invention, the cosmeceutical formulation is treated to contain more oxygen that would result under normal conditions. In this embodiment, the formulation can be partially saturated, saturate or supersaturated with oxygen.

A method of the invention can be effective for a variety of types of treatment, including, e.g., to aid in wound healing, treating sunburn or acne lesions, treating damage resulting from chemical peels, increasing skin moisturization, and/or reducing fine lines and wrinkles.

Advantages of the system and methods of the present invention include that it is readily portable, and can be administered by an individual without the help of trained personnel or pressurized oxygen tanks, and without the need to sterilize or maintain machines or other equipment. No surgery or injection is required. There is no risk of side effects. And immediate anti-age results can be attained.

As used herein, the term "about" refers to plus or minus 10% of the indicated value.

As used herein, the singular forms "a," "an" and "the" include plural referents unless the context clearly dictates otherwise.

Perfluorocarbons (PFC's)

Oxygen is necessary for proper cell metabolism. As one ages, the ability to diffuse oxygen to surrounding tissues decreases considerably. Therefore, processes like collagen and elastin production and waste removal become compromised. Without wishing to be bound by any particular mechanism, it is suggested that a PFC formulation of the invention adds much needed oxygen to the skin, resulting in a younger-looking, more radiant complexion.

Perfluorocarbons (PFC's) are a non-hazardous, colorless and odorless liquid material with a high capacity to transport gases, such as oxygen, nitrogen and carbon dioxide. The physical structure of PFC's is such that gases are entrapped inside their molecular structure. These gases are released by diffusion. When applied to the skin by a method of the invention, the PFC's increase moisture levels in the skin, promoting skin respiration and hydration and the reduction of fine lines and wrinkles.

Without wishing to be bound by any particular mechanism, it is suggested that PFC's can act to treat damaged skin (or to prevent damage to skin) and to reverse the signs of aging by any of a variety of possible mechanisms. For example, carbon dioxide is more soluble in the PFC's than oxygen; thus, when carbon dioxide is present in the skin, it may be taken up by the PFC's and the oxygen from the PFC's will be released. The purging of carbon dioxide from the skin cells allows the skin to breathe and be refreshed, resulting in a more youthful, even toned and healthy skin. Also, PFC's are di-electric by nature and may be able to hamper nerve impulses, which promote muscle contractions. Due to this di-electric property, when applied topically to the skin, PFC's may be able to relax superficial muscles, such a glabellar muscles, and therefore to produce similar effects as Botox. In addition, PFC's may function as dermal fillers due to their hydrophobic and lipophobic nature. The PFC's may position themselves between intracellular lipids and moisture in the skin, resulting in the agglomeration of the material to minimize its contact with water and lipids in the skin. This may volumize the dermis by creating a three-dimensional hexagonal micelle structure in the dermis, resulting in a wrinkle filling effect. Furthermore, treatment with a PFC mixture of the invention may add much needed nutrients to the skin, resulting in younger-looking, more radiant complexion; and oxygenation helps to kill skin surface bacteria, which keeps future breakouts to a minimum. The above effects may be referred to as dermal rejuvenation.

The formulation of PFC's used in a system or method of the invention generally comprises a mixture of three or more PFC molecules of different molecular weights that penetrate the skin at different times. The different half lives and variable molecular weights of the combined PFC's maximize the acting time in the dermis. Low molecular weight PFC's penetrate the dermis readily and quickly, while higher molecular weight PFC's penetrate more slowly, maintaining the initial result and further moisturizing the dermis. The PFC's may be a mixture of two or more of perfluoropropane, perfluorobutane, perfluoropentane, perfluorohexane, perfluorodecalin, perfluorodimethyl-cyclohexane, and perfluoroperhydrophenanthrene. The PFC's may be a combination of two or three of perfluorodecalin, perfluorohexane, and perfluoroperhydrophenanthrene. The PFC's may be a mixture of two or more of pentafluoro-propane, perfluorotripropylamine, C6-C9 perfluoroalkanes, perfluoroperhydrofluoranthrene, perfluorodecalin, perfluoroperhydrophenanthrene, bis(perfluor-hexyl)-1,2-ethene, perfluoro-1,3-dimethylcyclohexane, perfluoromethyldecalin, perfluoroisopropyldecalin, and/or a mixture of perfluoroperhydrophenanthrene and perfluoro n-butyl decalin). The PFC's may be a different combination among these groups.

Application of the PFC's of the invention increases the volume of the dermis by about 10-15%, reducing the appearance of wrinkles.

PFC's of the invention are medical grade, i.e. are biocompatible and are appropriate for use as in a topical composition which is administered to a subject, such as a human, e.g. to the face. All of the components of a cosmeceutical formulation of the invention are medical grade. In some embodiments (e.g. in which components such as lavender oil, which may contain allergens, are absent), the composition is non-allergenic.

Hyaluronic acid (HA)

HA is a skin hydrating agent that can help restore water to dehydrated skin. When applied according to a method of the invention, HA molecules can deliver substantially instant hydration to the skin.

HA is a non-sulfated glycosaminoglycan, naturally found in the human body and is the main component of the extracellular matrix. HA is found in high levels in the skin, where it is naturally produced by both fibroblasts and keratinocytes and exists as a polymer of medium molecular weight (600-1,000 kDa). An important function of HA is to hold water in the intercellular matrix of the connective tissue. This water-binding capacity significantly contributes to the elasticity of the skin, serving as a water reservoir. With aging and UV-B damage, the quantity and quality of hyaluronic acid in the skin decreases, which leads a loss of elasticity and the increase of wrinkles.

HA used in a formulation of the invention can be any of a variety of forms that will be evident to a skilled worker. These include, for example, salts (such as sodium salts, sodium hyaluronate) and derivatives that will be evident to a skilled worker The formulation of HA used in a system or method of the invention generally has a very low molecular weight, e.g.

about 100 kDa or less, about 50 kDa or less, or about 50 kDa. This low molecular weight allows for increased permeation through the skin compared to high molecular weight hyaluronic acid. The HA can rejuvenate the skin by improving its viscoelastic properties and significantly decreases deep wrinkles. HA is commercially available from a number of sources.

Additional Components

Skilled workers will recognize other, optional ingredients that can be added to a formulation of the invention. These include, e.g., conventional accelerators, niacin, vitamin E, vitamin C, or other vitamins, minerals, enzymes, amino acids, antioxidants, blood dilating ingredients, and natural enjoyable fragrances. For example, additional components can include one or more of HSC (Hydrophobic Sphingolipid Complex), which restores the stratum corneum, allowing the isolation of the skin moisture; Atoxelene, which reduces fine lines and wrinkles; Retistar™ (stabilized retinol), an antioxidant blend which is a highly effective substance for the care of aging skin and protects against photo-aging; a Light/Natural Fragrance, such as rose floral water, which soothes and regenerates the skin, vanilla floral water, which tones and revitalizes skin, or prickly pear, which locks moisture into the skin.

In embodiments of the invention, additional optional ingredients can include one or more of the following, e.g. in approximately the range of concentrations as noted:

Intracellular oxygen boosters, such as, e.g., Cerasome Oxygen (a ceramide based delivery system containing molecular oxygen which is distributed by ROVI cosmetics), or *Tropaeolum Majus* Flower/Leaf/Stem Extract (0.005-30%);

Emulsifiers, such as nonionic, cationic, anionic or polymeric emulsifiers, including, e.g., glyceryl stearate, cetearyl alcohol, cetearyl phosphate, behentrimonium chloride, polysorbate-20, acrylaytes/C10-30 alkyl acrylate crosspolymer, etc (0.1-20%);

Rheology modifiers, including, e.g., polyacrylic acid polymers, xanthan gum, cellulose gums, silicates, alginates, hydrocolloids, etc (0.05-5%);

Humectants, such as, e.g., propanediol, glycerin and other glycols, including butylene glycol (0.5-8%);

Surfactants, including, e.g., cationic and anionic, ethoxylated and non-ethoxylated, and amino acid surfactants, including polysorbate 20, sorbitan monooleate, or sodium lauroyl glutamate (0.1-5%);

Emollients, such as, e.g, squalane, ethylhexyl palmitate, diisopropyl dimer dilinoleate, C12-15 Alkyl Benzoate, or *Melalenca alternifolia* (Tea Tree Leaf) (0.1-20%);

pH modifiers, such as, e.g., triethanolamine, sodium hydroxide, acidifiers, including citric acid (0.005-2%);

Antimicrobial agents, such as, e.g., salicylic acid, or preservatives, such as, e.g., phenoxyethanol, benzyl alcohol, or potassium sorbate (0.001-3%);

Aromas, in the form of fragrances or essential oils (0.005-5%);

Antioxidants, such as, e.g., ascorbic acid or derivatives thereof, including ascorbyl palmitate, ascorbyl glucoside, ascorbyl isostearate, sodium ascorbyl phosphate, magnesium ascorbyl phosphate, ethyl ascorbic acid, or aminopropyl ascorbyl phosphate; or tocopherol of derivatives thereof, including tocopheryl acetate, tocopheryl oleate, or tocopheryl linoleate.

Skin care antiaging agents, such as, e.g., licorice extract and derivatives, Retistar™ (stabilized retinol) (0.005-5%, e.g. 0.5-1%);

Suitable buffers.

In addition, the following components can be included in formulations for specific uses.

For acne treatment (for adults), an effective amount of salicylic acid (e.g., 0.001-3%) can be included.

For treatment of cellulite, effective amounts of agents to regulate adipocyte metabolism, such as, e.g., well-known adipogenesis inhibitors, lipogenesis inhibitors, or lipolytic agents (0.005-20%) can be included. These include, e.g., various agents, some of which are available in different combinations in commercially available blends that will be evident to skilled workers, including, e.g., butylene glycol, chenopodium quinoa seed extract, caffeine, sodium salicylate, lysolecithin, hydrogenated lecithin, aspartame, glycine soja germ extract, silica, *Coleus forskohlii* root extract, *Coffea arabica* seed extract, glycerin, *Nephelium longana* seed extract.

For the use as a foundation for make-up, suitable colorants such as e.g., FD&C colors (colors which are certified and allowed by the US for the Food, Pharmaceutical, Cosmetics & Personal Care industry), iron oxides, titanium dioxides, including silicon-treated pigments, (0.001-30%) can be included, in the form of powder particle or pre-dispersions in various dispersants, such as castor oil, silanetriol, silicone, hydroxystearic Acid, mineral oils, or $C_{12}$-$C_{15}$ alkyl benzoate.

Among the components which can be absent in a cosmeceutical formulation of the invention are, e.g., perfluorodimethylcyclohexane; alcohols; silicone surfactants, fluoro surfactants, or mixtures thereof; volatile silicone, perfluoroalkyl denatured silicone; perfluoroalkyl denatured methylphenyl polysiloxane; colloidal metal; carnitine derivatives; sunscreens; 2-hydroxyalkanoic acid having from 3-20 carbon atoms; spermine or other polyamines, or unbranched aliphatic polyazamine.

Table 1 below shows an exemplary preparation of a PFC/HA formulation of the invention. Methods for combining these components are conventional and well-known in the art.

TABLE 1

AN EXEMPLARY FORMULATION

| | |
|---|---|
| medical grade Perfluorocarbons (gas carriers, including Perfluorohexane, perfluoroperhydrophenanthrene, perfluorodecalin, perfluorodimethylcycloheane) | 0.005 to 30% |
| intracellular oxygen diffusion booster (*Tropaeolum Majus* Flower/Leaf/Stem Extract) | 0.005 to 30% |
| kilodalton-range Hyaluronic Acid (50 kDa) | 0.005 to 5% |
| emulsifiers Non ionic Cationic, Anionic & polymeric (including glyceryl stearate, cetearyl alcohol, Cetearyl Phosphate, Behentrimonium Chloride, Acrylates/C10-30 Alkyl Acrylate Crosspolymer, etc) | 0.1 to 20% |
| rheology modifiers (including polyacrylic acid polymers, xanthan gum, cellulose gums, silicates, alginates, hydrocolloids, etc) | 0.05 to 5% |
| humectant (including propanediol, glycerin & other glycols) | 0.5 to 5% |
| surfactants (Nonionic Cationic and Anionic, Ethoxylated and Non Ethoxylated) | 0.1 to 5% |

TABLE 1-continued

AN EXEMPLARY FORMULATION

| | |
|---|---|
| emollients | 0.1 to 20% |
| antioxidants | 0.005 to 5% |
| pH modifier | 0.005 to 2% |
| antimicrobial agents (such as salicylic acid, and preservatives) | 0.001 to 3% |
| colorants (including FD& C colors, iron oxides, titanium dioxides; including silicon-treated pigments) | 0.001 to 30% |
| aroma (fragrance or essential oils) | 0.005 to 5% |
| Adipocyte metabolism regulating agent (adipogensis inhibitor, lipogensesis inhibitor, lipolytic agent) | 0.005-20% |
| Propellant (liquefied hydrocarbon of 1 to 10 carbon atoms, such as n-propane, n-butane, isobutene, isopentane, n-pentane and mixture) and/or ethers (dimethyl ether), nitrogen or compressed air. | 5-20% |

Manufacturing Procedure:

Combine the preceding components by conventional methods. Add to a suitable container as a pressurized aerosol with liquefied propellant at a desired ratio (e.g., about 5-20%). The propellant can be, e.g., a liquified hydrocarbon of 1 to 10 carbon atoms, such as n-propane, n-butane, isobutene, isopentane, n-pentane and mixture and/or an ether (e.g., dimethyl ether), nitrogen, compressed air, or other inert gas.

Another exemplary formulation is shown in Table 2:

TABLE 2

| INGREDIENTS INCI/CTFA NAME | APPROXIMATE % W/W |
|---|---|
| Phase A (Water phase) | |
| Water (Aqua) | 57.500 |
| Phenoxyethanol | 0.500 |
| Ethanol | 15.000 |
| Glycereth-26 | 3.000 |
| Hydrolyzed Hyaluronic Acid | 1.000 |
| Tropaeolum Majus Flower/Leaf/Stem Extract | 1.000 |
| Phospholipids | 1.000 |
| Polysorbate 20 | 1.000 |
| Phase B (Oil phase) | |
| Polydecene | 2.500 |
| Isododecane | 7.500 |
| Phase C (PFC's) | |
| Perfluorodecalin | 5.000 |
| Perfluorohexane | 2.500 |
| Perfluoroperhydrophenanthrene | 2.500 |
| | 100.000 |

Manufacturing Procedure:

Combine water and oil phase, homogenize and mix until uniform, then add Perfluorocarbons. Add to a suitable container as a pressurized aerosol with liquefied propella (e.g., about 5-20%). The propellant can be, e.g., a liquefied hydrocarbon of 1 to 10 carbon atoms n-butane, isobutene, isopentane, n-pentane and mixture and/or an ether (e.g., dimethyl ether), ni compressed air, or other inert gas.

Another exemplary formulation is shown in Table 3:

TABLE 3

| INGREDIENTS INCI/CTFA NAME | APPROXIMATE % W/W |
|---|---|
| Phase A (Water phase, 82.95%) | |
| Water (Aqua) | 72.150 |
| Ethylhexylglycerin | 1.000 |
| Phenoxyethanol | 1.000 |
| Propanediol | 5.000 |
| Hydrolyzed Hyaluronic Acid | 1.000 |
| Tropaeolum Majus Flower/Leaf/Stem Extract | 2.000 |
| Phospholipids | 0.500 |
| Acrylates/C10-30 Alkyl Acrylate Crosspolymer | 0.300 |
| Phase B (Oil phase, 12.55%) | |
| Glyceryl Stearate | 1.000 |
| Cetearyl Alcohol | 0.500 |
| Stearic Acid | 1.000 |
| Sodium Lauroyl Glutamate | 0.100 |
| Neopentyl Glycol Diheptanoate | 1.000 |
| Isododecane | 4.000 |
| Cyclopentasiloxane | 3.000 |
| Cyclohexasiloxane | 1.000 |
| Dimethicone | 0.500 |
| Sodium Hydroxide | 0.100 |
| Tocopheryl Acetate | 0.100 |
| Retinyl Palmitate | 0.100 |
| Ascorbyl Palmitate | 0.100 |
| Phase C (PFC's, 4.5%) | |
| Chamomile Oil | 0.050 |
| Perfluorodecalin | 2.500 |
| Perfluorohexane | 1.250 |
| Perfluoroperhydrophenanthrene | 0.750 |
| | 100.000 |

Manufacturing Procedure:

Combine water and oil phase and heat to 60-80° C., add oil to water, homogenize and mix until uniform and cool to room temp and add perfluorocarbons and fragrance. Add to a suitable container as a pressurized aerosol with liquefied propellant at a desired ratio (e.g., about 5-20%). The propellant can be, e.g., a liquified hydrocarbon of 1 to 10 carbon atoms, such as n-propane, n-butane, isobutene, isopentane, n-pentane and mixture and/or an ether (e.g., dimethyl ether), nitrogen, compressed air, or other inert gas.

In one embodiment of the invention, a cosmeceutical formulation of the invention is partially saturated, saturated, or supersaturated with oxygen before it is packaged under pressure in a closed container, to be delivered as an aerosol. In this embodiment, either the mixture of PFCs or the final formulation is treated to contain more oxygen that would result under normal conditions.

In one embodiment, the PFC component or the final cosmeceutical formulation of the invention is saturated with oxygen. In this embodiment, the concentration of oxygen is at least about 0.3 ml of oxygen (STP) per one ml of the PFC component or final formulation at 1 atmosphere. The partial pressure of oxygen, or $pO_2$, in the formulation is generally above 760 mm Hg in this embodiments.

In another embodiment, the PFC component or the final cosmeceutical formulation is supersaturated with oxygen. In this embodiment, the concentration of oxygen is at least about 1 ml of oxygen (STP) per one ml of the PFC component or formulation. In another embodiment, the concentration of oxygen is at least about 2 ml of oxygen (STP) per ml of the PFC component or formulation. The partial pressure of oxygen, or $pO_2$ in the emulsion is generally above 10,000 mm Hg, and can be as high as 11,000 mm Hg or higher.

Methods for introducing the added oxygen to the PFC component or cosmeceutical formulation of the invention are conventional. For example, the PFC component of the formulation or the complete formulation can be exposed to oxygen under conditions sufficient to gasify the emulsion to a predetermined degree. It may be exposed to oxygen under atmospheric pressure or under a pressure that is above atmospheric pressure. For example, it may be exposed to oxygen under 180 psi for sufficient time to achieve $pO_2$ in the solution of at least about 10,000 mm Hg.

Whether or not additional oxygen is added to a cosmeceutical formulation of the invention, the cosmeceutical formulation is preferably stored under pressure in a container (e.g. a dispensing bottle) to prevent oxygen dissolution and escape from the formulation. In addition, the pressurized container can maintain the phase equilibria between the solubilized oxygen in the formulation and the pressurized oxygen. In one embodiment, the pressurized container holding the formulation should maintain an internal pressure that, at a minimum, remains equal to or greater than the equivalent dissolved oxygen partial pressure. Also, in one embodiment, the pressurized container allows full dispensation of the gas delivery agent, e.g. the PFC mixture, (greater than 95% of total charging weight dispensed).

Device for Application

Devices that are suitable for packaging and delivering formulations of the invention include aerosol bottles in the 0.5-10 oz range. In one embodiment of the invention, the device is a propellant-powered hand-held system, such as an aluminum canister with a directional nozzle. The materials used in an applicator of the invention can be optimized using conventional procedures, to ensure that they are compatible with the PFC/HA formulation. Propellants at conventional concentrations, e.g., 5-25% propellant, such as A-17 propellant or others described above, can be used. In other embodiments of the invention, the device is a plastic bottle which utilizes a pump spray, or a glass bottle which utilizes a pump spray. Using such devices, a formulation of the invention can be sprayed directly onto areas to be treated, such as crow's feet, laugh lines, forehead furrows, and other areas which would benefit, e.g., from immediate plumping and hydration.

Methods for Applying a Cosmeceutical Formulation of the Invention

In embodiments of the invention, the cosmeceutical formulation of the invention is applied twice a day, as an aerosol preparation, for example to the face. In one embodiment, the container (such as a bottle) is first shaken well. Prior to use, the applicator is primed by spraying about 3 times, away from the face. The user then presses the actuator button and dispenses about three stripes on the right side of the face (cheekbone, mouth to ear, and jaw line) and immediately massages. This procedure is repeated on the left side. About one stripe is then dispensed across the forehead and massaged.

In general, contact with the eyes and lips is to be avoided. In some cases, the product may cause the skin to tingle and flush slightly for a short time. If discomfort occurs, the user is cautioned to avoid spraying directly onto the face. Instead, the user should dispense the product onto the fingertips and massage gently onto face and forehead using his or her fingers. Mild skin irritation may occur in some users. If irritation occurs, it is recommended that the user reduce the frequency of application to once a day, or once every other day; and, if irritation becomes severe, discontinue use and consult a doctor.

It will be evident to those skilled in the art that other methods, sometimes in conjunction with a spray device as above, may be used to apply a combination hyaluronic acid/PFD formulation of the invention. For example, the formulation can be applied, with our without the aerosol application, in combination with a Bliss® triple oxygen instant energizing mask, which provides a foaming action. Other suitable methods of administration include osmotic pressurized devices which are pressure cans that contain ingredients that can be sprayed onto a patient's face; or osmotic nebulizers, which have either small hand pieces that mist or spray a solution onto to the skin or a full face mask that goes over the face and mists the solution onto the skin. Such a device has a small bowl (e.g. a plastic bowl) that the solution or ampoule is poured into, and is then sprayed over the skin. Another suitable delivery device uses electro ionization.

In another embodiment of the invention, a cosmeceutical formulation of the invention is administered, not as an aerosol, but as a serum, foaming agent, mist or cream.

In the foregoing and in the following examples, all temperatures are set forth in uncorrected degrees Celsius; and, unless otherwise indicated, all parts and percentages are by weight.

EXAMPLES

Example I

Clinical studies were conducted, in which a cosmeceutical composition of the invention was applied to subjects as an aerosol, and the results were analyzed immediately, 2 weeks or 4 weeks after application. Some of the results are shown in FIG. 1.

After just one use, clinical instruments measured up to a 130% increase in moisture in the skin. After two weeks, 83% of the women tested reported that their lines appeared to be dramatically smoother and softer. 90% of the women reported an improvement in their skin's appearance overall.

Example II

A Detailed Account of the Experiments Summarized in Example I

Controlled Usage Study to Evaluate Tolerance and Efficacy of an Anti-Aging Product Formula #176-64C-6 from Kate Somerville Skin Care was tested. Wrinkle assessment was conducted instrumentally using a SKIN REPLICA image analysis system. Elasticity and viscoelastic properties of the skin were measured as a function of flexibility and firmness employing a Cutometer. Retained water content of the skin was measured using the Nova Dermal Phase Meter. In addition, product effectiveness was subjectively evaluated using panelist self-assessment via questionnaire responses.

Test Material:

Inclusion criteria: Female subjects between the ages of 35 and 55 were in general good health and free of any health problems, including neurological, dermatological, or systemic disorder that would interfere with the results. Individuals experiencing facial wrinkles, loss of firmness and dryness were selected. Individuals abstained from using any anti-aging or moisturizing products for a period of 72 hours prior to study commencement and used only the assigned test material during the test period.

Exclusion criteria: The study excluded individuals under the care of a physician. individuals taking medication that may mask or interfere with the test results, individuals diagnosed with chronic skin allergies, individuals who have had Botox procedure, individuals who are pregnant, lactating, have been pregnant, or given birth within the six month period immediately preceding study commencement, subjects with a history of any form of skin cancer, melanoma, lupus, psoriasis, connective tissue disease, diabetes, or any disease that would increase the risk associated with study participation, individuals with irritation or sensitivity to any cosmetic products, individuals with known allergies or skin and/or eye conditions.

Population Demographics:

| | | |
|---|---|---|
| Number of subjects enrolled | | 30 |
| Number of subjects completing study | | 30 |
| Age Range | | 37-55 |
| Sex | Female | 30 |
| Race | Caucasian | 30 |

Procedure:

Prior to study commencement all panelists were instructed to cleanse their face using a gentle cleanser (Cetaphil) with warm water being certain to rinse well. The subjects were than acclimated to the ambient environment (70° F.±2° and 40%±2% relative humidity) for a period of thirty minutes prior to test product application. The areas of involvement were marked on the facial surface using a standard template, to ensure that instruments are repositioned in the same place at each visit.

Subjects were instructed to apply the test product according to following instruction:

AM/PM Use twice daily. Shake bottle well. Prior to use, prime the applicator by spraying three times away from face, shaking the bottle again in between each spray. Hold applicator ½" from right side of face. Press actuator button to dispense formula in three horizontal stripes across the right side of the face only: once across cheekbone, once from mouth to ear, and once across jaw line. Immediately massage product into face and neck thoroughly. Shake bottle well again. Repeat steps on left side of face. Massage product into face and neck thoroughly. Shake bottle well again and apply one horizontal stripe to forehead. Massage in thoroughly.

The biophysical measurements (Skin Moisturization [Electroconductivity] via Novameter and Skin Elasticity via Cutometer) as well as Skin Replica Impressions were collected at baseline, immediately (10 minutes) after the initial application and again after 2 and 4 weeks of use. The initial application of the test material took place in the testing facility. All study participants were asked to fill out a self-assessment questionnaire immediately after the initial application and again after 2 and 4 weeks of use.

The following distinct noninvasive methods were employed to establish evaluation parameters:

Electroconductivity—Skin Moisturization Via Novameter:

A Nova Dermal Phase Meter, Model DPM 9003 (Nova, Technology Corp., Gloucester, Mass.) was used to obtain measurements of skin surface impedance to determine electroconductivity of the treatment sites. This meter provides a relative measure of the retained water content of the skin as a function of the skin's dielectric value. Skin impedance was recorded automatically when equilibrium was achieved.

Skin Elasticity Via Cutometer:

A Cutometer SEM 575 (model 575 Courage+Khazaka) was used to measure skin viscoelastic properties. The measuring principle is based on a suction method. Negative pressure is created in the device, which can be regulated between 20 and 500 mbar. Skin is drawn into a calibrated aperture of the probe by negative pressure where skin penetration depth is determined by a non-contact optical measuring system. The optical measuring system consists of a light transmitter and a light recipient, as well as two glass prisms facing each other, which project the light from transmitter to recipient. The light intensity varies due to the penetration depth of the skin.

Profilometry of Living Skin—Skin Replica Image Analysis

REPLICA™ brand locators are specifically designed for making silastic casts of the skin surface for the purpose of assessing texture and wrinkles. The Large Area Locator is specially designed for obtaining replicas of skin contour for assessing cellulite. The heavy weight paper and foam adhesive system gives firm support to the cured replica while maintaining a level of conformability to the general contour of the test site. Locators have a large write-on tab area for sample identification and die cut notches for accurate positioning.

REPLICA™ SAMPLING TECHNIQUE: After peeling the Locator from the carrier sheet, the adhesive side is placed against the skin; pre-mixed resin (SILFLO or REPLIFLO) is placed in the interior and smoothed out with a wooden spatula so that the resin overflows 2-3 mm onto the cardboard surface. After the resin has cured and the replica peeled from the skin surface, the foam adhesive spacer layer is separated from the cardboard frame and discarded. Image Analysis can be easily performed with the replica.

REPLICA™ samples were analyzed using a computerized image analysis technique for converting visual information about skin into numeric data.

REFERENCES FOR ANALYTICAL METHODS

1. Leveque, J. L., de Rigal, J.: Impedance Methods for Studying Skin Moisturization, J. Soc. Cosmet. Chem., 34: 419-428, 1983.
2. Agache, P. G., Monneur, C., Leveque, J. L., and de Rigal, J. Mechanical properties and Young's modulus of human skin in-vivo, *Arch. Dermatol. Res.*, 269, 221, 1980.
3. De Rigal, J. and Leveque, J. J., In vivo measurement of the stratum corneum elasticity, *Bioeng. Skin*, 1, 13, 1985.
4. Profilometry of skin—A useful tool for the substantiation of cosmetic efficacy, Cook, J Soc Cosmet Chem 1980; 31:339-359.
5. Optical profilometry: An objective method for quantification of facial wrinkles, Grove, Grove, and Leyden. J AM ACAD DERMATOL 1989; 21:631-7.
6. Treatment of photodamaged facial skin with topical tretinoin, Leyden et al. JAM ACAD DERMATOL 1989; 21:638-44.
7. Roughness (measured by profilometry: mechanical, optical, and laser), Muller, in "Bioengineering and the Skin: Methods and Instrumentation" Berardesca et al, Eds. CRC Press, Boca Raton, 1995.
8. Review articles from "Handbook of Non-Invasive Methods and the Skin", Serup and Jemec, Eds. CRC Press, Boca Raton, 1995.
   Stylus method for skin surface contour measurement, Gassmuller et al p 83.

Skin surface replica image analysis of furrows and wrinkles, Corcuff and Leveque, p 89.
Laser Profilometry, Elfsen et al, p 97
Three dimensional evaluation of skin surface: micro and macro-relief, Mignot, p 107.

The source data were:

Subjective assessments collected 15 minutes after initial application and again after 14 and 28 days of twice daily use of the test product. Novameter readings collected prior to initial application, 10 minutes after initial application and again after 14 and 28 days of twice daily use of the test product.

Cutometer readings collected prior to initial application and 10 minutes after initial application and again after 14 and 28 days of twice daily use of the test product.

Skin Replicas collected prior to initial application and 10 minutes after initial application and again after 14 and 28 days of twice daily use of the test product.

Results are given in the Tables and figures. No adverse effects or unexpected reactions of any kind were observed on any of the subjects.

Conclusions: The test material was reported by the majority of test panelists to be an effective anti-aging product improving overall condition of the skin. Subjective questionnaire responses indicated that at the end of the study the product left their skin looking and feeling more hydrated, firmer, radiant, more even, softer and smoother. Additional instrumental analysis performed for the test product demonstrated increases in skin moisture content on the site treated with the product. Demonstrated increases in mean moisturization values are considered statistically significant at each evaluation time point.

TABLE 4

Moisturization Study - Electroconductivity via Novameter
Moisturization Study - Electroconductivity via Novameter
Client No.: Formula #: 176-64C.6

| Study Time Point: | 15 Minutes | 14 days | 28 Days |
|---|---|---|---|
| % Difference: | 38.46%* | 20.53%* | 26.22%' |
| Max % Improvement: | 131.52% | 55.88% | 65.05% |

*Statistically Significant

Cutometer readings demonstrated that the test material increased the skin elasticity as a function of firmness. The increases are considered statistically significant.

TABLE 5

Skin Elasticity via Cutometer
Skin Elasticity via Cutometer (R7)
Client No.: Formula #: 176-64C-6

| Study Time Point: | 15 Minutes | 14 days | 28 Days |
|---|---|---|---|
| % Difference: | 4.08%* | 8.17%* | 12.01%* |
| Max % Improvement: | 12.83% | 20.71% | 21.67% |

*Statistically Significant

Skin replica image analysis results demonstrated that the test material statistically significantly improved the condition of wrinkles at the 10 minute time point, with 63% of the panel exhibiting smoothing of the wrinkles according to the three key parameters. At the week 2 and week 4 time points a majority of 56% and 59% of the panel exhibited smoothing of the wrinkles for the three key parameters.

Instrumental analysis (Novameter, Cutometer and Skin Replica Image Analysis) corroborated information obtained from subjective questionnaires.

Electroconductivity Via Novameter

Figure 2:
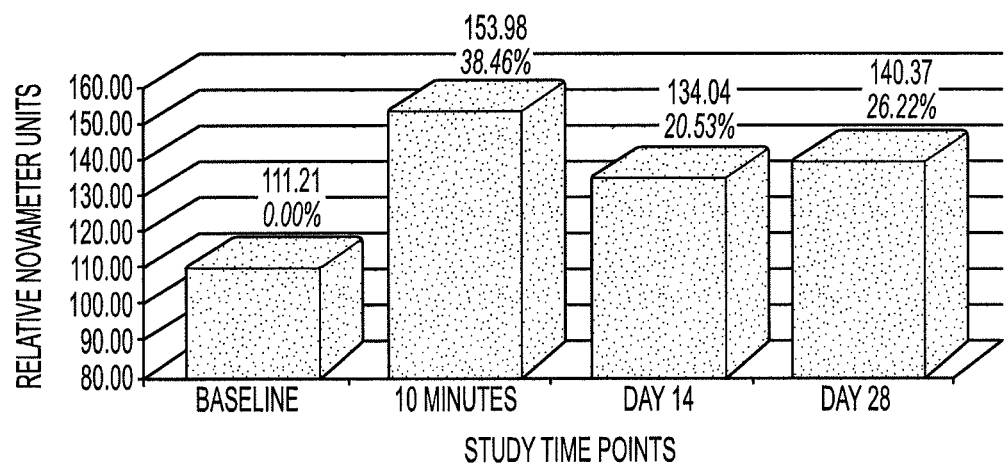
FIG. 2 shows electroconductivity via novameter measurements.

A Nova Dermal Phase Meter, Model DPM 9003 (Nova, Technology Corp., Gloucester, Mass.) was used to obtain measurements of skin surface impedance to determine electroconductivity of the test sites. This meter provides a relative measure of the retained water content of the skin as a function of the skin's dielectric value. Skin impedance was recorded automatically when equilibrium was achieved. The data are shown in Table 6 and are presented graphically in FIG. 2.

Skin Elasticity Via Cutometer

Figure 3:
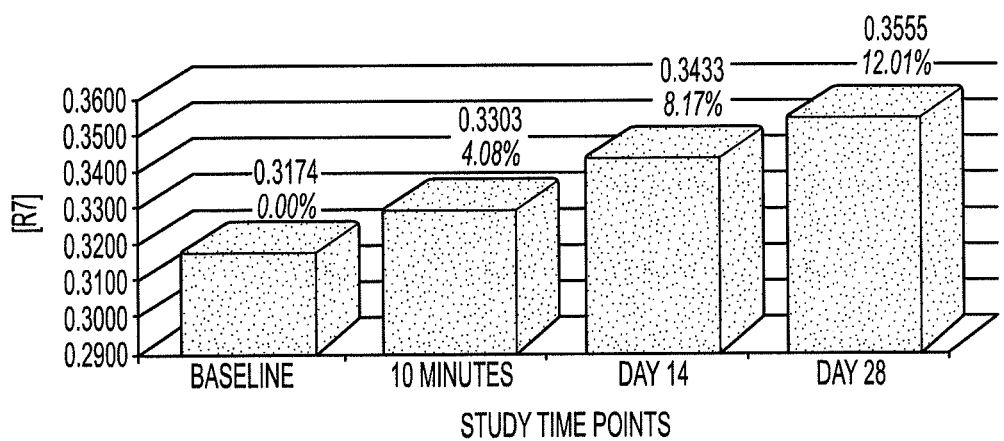
FIG. 3 shows skin elasticity via cutometer measurements.

A Cutometer SEM 575 (model 575 Courage+Khazaka) was used to measure skin viscoelastic properties. The measuring principle is based on a suction method. Negative pressure is created in the device, which can be regulated between 20 and 500 mbar. Skin is drawn into a calibrated aperture of the probe by negative pressure where skin penetration depth is determined by a non-contact optical measuring system. The optical measuring system consists of a light transmitter and a light recipient, as well as two glass prisms facing each other, which project the light from transmitter to recipient. The light intensity varies due to the penetration depth of the skin. The data are shown in the Table 7 are presented graphically in FIG. 3

TABLE 6

Electroconductivity via Novameter
MOISTURIZATION STUDY - ELECTROCONDUCTIVITY VIA NOVAMETER
Sample No.: M-2666
Client No.: #: 176-64C-6

| Panelist ID No.: | Baseline | 10 Minutes | Individual % Difference | Day 14 | Individual % Difference | Day 28 | Individual % Difference |
|---|---|---|---|---|---|---|---|
| 52 3397 | 118.67 | 148.00 | 24.72% | 123.33 | 3.93% | 131.33 | 10.67% |
| 50 5957 | 100.00 | 10.67 | 30.67% | 112.67 | 12.67% | 114.00 | 14.00% |
| 11 8412 | 105.33 | 126.67 | 20.26% | 122.00 | 15.83% | 119.33 | 13.29% |
| 54 2855 | 116.33 | 269.33 | 131.52% | 181.33 | 55.88% | 192.00 | 65.05% |
| 56 5116 | 96.67 | 140.67 | 45.52% | 131.33 | 35.85% | 114.67 | 18.62% |
| 44 8978 | 113.33 | 150.67 | 32.95% | 136.67 | 20.59% | 153.33 | 35.30% |
| 54 8532 | 113.33 | 130.00 | 14.71% | 130.67 | 15.30% | 136.67 | 20.59% |
| 54 7549 | 106.67 | 138.00 | 29.37% | 132.00 | 23.75% | 120.00 | 12.50% |
| 68 7601 | 130.00 | 150.67 | 15.90% | 131.33 | 1.02% | 144.67 | 11.28% |
| 66 0675 | 105.33 | 140.00 | 32.92% | 133.33 | 26.587% | 162.67 | 54.44% |
| 40 6591 | 104.67 | 153.33 | 46.495 | 120.00 | 14.65% | 128.67 | 22.93% |
| 52 8160 | 102.00 | 160.00 | 56.86% | 146.00 | 43.14% | 127.33 | 24.83% |
| 62 0956 | 104.00 | 137.33 | 32.05% | 142.67 | 37.18% | 156.00 | 50.00% |
| 60 2360 | 104.00 | 166.00 | 59.62% | 135.33 | 30.13% | 125.33 | 20.51% |

TABLE 6-continued

Electroconductivity via Novameter
MOISTURIZATION STUDY - ELECTROCONDUCTIVITY VIA NOVAMETER
Sample No.: M-2666
Client No.: #: 176-64C-6

| Panelist ID No.: | Baseline | 10 Minutes | Individual % Difference | Day 14 | Individual % Difference | Day 28 | Individual % Difference |
|---|---|---|---|---|---|---|---|
| 48 5450 | 99.33 | 181.33 | 82.55% | 122.00 | 22.82% | 126.67 | 27.52% |
| 50 7599 | 102.67 | 134.67 | 31.17% | 110.67 | 7.79% | 116.67 | 13.64% |
| 66 6453 | 130.67 | 142.00 | 8.67% | 134.67 | 3.06% | 135.33 | 3.57% |
| 48 1570 | 122.67 | 130.00 | 5.98% | 123.33 | 0.54% | 129.67 | 5.71% |
| 62 3461 | 138.00 | 166.00 | 20.29% | 159.33 | 15.46% | 164.00 | 18.84% |
| 60 8470 | 131.33 | 184.67 | 40.62% | 150.67 | 14.73% | 163.33 | 24.37% |
| 64 0508 | 118.00 | 146.00 | 23.73% | 142.00 | 20.34% | 138.00 | 16.95% |
| 58 6382 | 116.00 | 146.67 | 26.44% | 137.33 | 18.39% | 160.00 | 37.93% |
| 58 7856 | 114.00 | 123.33 | 8.18% | 125.33 | 9.94% | 124.00 | 8.77% |
| 48 9034 | 103.33 | 145.33 | 40.65% | 140.00 | 35.49% | 142.00 | 37.42% |
| 50 6361 | 110.00 | 154.67 | 40.61% | 119.33 | 8.48% | 152.00 | 38.18% |
| 54 4374 | 102.67 | 178.67 | 74.02% | 142.67 | 38.96% | 162.67 | 58.44% |
| 60 5745 | 115.33 | 182.67 | 58.39% | 145.33 | 26.01% | 142.00 | 23.12% |
| 52 0789 | 107.33 | 168.00 | 56.53% | 143.33 | 33.54% | 159.33 | 48.45% |
| 54 4039 | 106.00 | 132.00 | 24.53% | 121.33 | 14.46% | 130.67 | 23.27% |
| 68 5881 | 98.67 | 162.00 | 64.18% | 125.33 | 27.02% | 138.67 | 40.54% |
| Mean: | 111.21 | 153.98 | | 134.04 | | 140.37 | |
| % Difference | | 38.46% | | 20.53% | | 26.22% | |
| p | | 0.000* | | 0.000* | | 0.000* | |
| t | | 8.227* | | 51.106* | | 9.098* | |

*Statistically Significant

TABLE 7

Skin Elasticity via Cutometer Formula #176-64C-6
SKIN ELASTICITY VIA CUTOMETER (R7)
Sample No.: M-2666
Client No.: Formula #: 176-64C-6

| Panelist ID No.: | Baseline | 10 Minutes | Individual % Difference | Day 14 | Individual % Difference | Day 28 | Individual % Difference |
|---|---|---|---|---|---|---|---|
| 52 3397 | 0.3421 | 0.3491 | 2.05% | 0.3483 | 1.81% | 0.3565 | 4.21% |
| 50 5957 | 0.3104 | 0.3171 | 2.16% | 0.3560 | 14.69% | 0.3561 | 14.72% |
| 11 8412 | 0.3698 | 0.3559 | −3.76% | 0.4174 | 12.87% | 0.4276 | 15.63% |
| 54 2855 | 0.3406 | 0.3557 | 4.43% | 0.3534 | 3.76% | 0.3829 | 12.42% |
| 56 5116 | 0.2649 | 0.2626 | −0.87% | 0.2947 | 11.25% | 0.3008 | 13.55% |
| 44 8978 | 0.2672 | 0.2778 | 3.97% | 0.2704 | 1.20% | 0.2799 | 4.75% |
| 54 8532 | 0.3104 | 0.3052 | −1.68% | 0.2853 | −8.09% | 0.3031 | −2.35% |
| 54 7549 | 0.2214 | 0.2413 | 8.99% | 0.2604 | 17.62% | 0.2677 | 20.91% |
| 68 7601 | 0.2104 | 0.2095 | −0.43% | 0.2221 | 5.56% | 0.2345 | 11.45% |
| 66 0675 | 0.3004 | 0.2999 | −0.17% | 0.3538 | 17.78% | 0.3655 | 21.67% |
| 40 6591 | 0.3305 | 0.3564 | 7.84% | 0.3563 | 7.81% | 0.3597 | 8.84% |
| 52 8160 | 0.4011 | 0.3983 | −0.70% | 0.3881 | −3.24% | 0.3992 | −0.47% |
| 62 0956 | 0.2147 | 0.2192 | 2.10% | 0.2162 | 0.70% | 0.2313 | 7.73% |
| 60 2360 | 0.3517 | 0.3722 | 5.83% | 0.3678 | 4.58% | 0.3890 | 10.61% |
| 48 5450 | 0.4500 | 0.4860 | 8.00% | 0.4922 | 9.38% | 0.4998 | 11.07% |
| 50 7599 | 0.3124 | 0.3446 | 10.31% | 0.3758 | 20.29% | 0.3800 | 21.64% |
| 66 6453 | 0.2998 | 0.2996 | −0.07% | 0.2963 | −1.17% | 0.3142 | 4.80% |
| 48 1570 | 0.2476 | 0.2585 | 4.40% | 0.2720 | 9.85% | 0.2864 | 15.67% |
| 62 3461 | 0.2297 | 0.2242 | −2.39% | 0.2384 | 3.79% | 0.2746 | 19.55% |
| 60 8470 | 0.3265 | 0.3451 | 5.70% | 0.3643 | 11.58% | 0.3795 | 16.23% |
| 64 0508 | 0.3378 | 0.3717 | 10.03% | 0.4078 | 20.71% | 0.3994 | 18.24% |
| 58 6382 | 0.4038 | 0.4234 | 4.86% | 0.4481 | 10.97% | 0.4583 | 13.50% |
| 58 7856 | 0.2701 | 0.2771 | 2.59% | 0.2968 | 9.89% | 0.3154 | 16.77% |
| 48 9034 | 0.4162 | 0.4046 | −2.79% | 0.4132 | −0.72% | 0.4229 | 1.61% |
| 50 6361 | 0.3749 | 0.3968 | 5.84% | 0.4211 | 12.32% | 0.4419 | 17.87% |
| 54 4374 | 0.4540 | 0.4978 | 9.65% | 0.4730 | 4.19% | .4898 | 7.89% |
| 60 5745 | 0.2937 | 0.3261 | 11.02% | 0.3375 | 14.90% | 0.3567 | 21.43% |
| 52 0789 | 0.3594 | 0.4055 | 12.83% | 0.4190 | 16.58% | 0.4203 | 16.94% |
| 54 4039 | 0.2489 | 0.2583 | 3.78% | 0.2552 | 2.53% | 0.2719 | 9.24% |
| 68 5881 | 0.2611 | 0.2706 | 3.64 | 0.2985 | 14.32% | 0.3003 | 15.01% |

TABLE 7-continued

Skin Elasticity via Cutometer Formula #176-64C-6
SKIN ELASTICITY VIA CUTOMETER (R7)
Sample No.: M-2666
Client No.: Formula #: 176-64C-6

| Panelist ID No.: | Baseline | 10 Minutes | Individual % Difference | Day 14 | Individual % Difference | Day 28 | Individual % Difference |
|---|---|---|---|---|---|---|---|
| Mean: | 0.3174 | 0.3303 | | 0.3433 | | 0.3555 | |
| % Difference | | 4.08% | | 8.17% | | 12.01% | |
| p | | 0.000* | | 0.000* | | 0.000* | |
| t | | 4.430* | | 23.150* | | 9.949* | |

*Statistically Significant

TABLE 8

SKIN REPLICA IMAGE ANALYSIS - DATA LISTING

| Time Point | Panelist ID No.: | Rz | IDL | NumWr | Panelist ID No.: | Rx | IDL | NumWr | Panelist ID No.: | Rz | IDL | NumWr |
|---|---|---|---|---|---|---|---|---|---|---|---|---|
| Baseline | 52 3397 | 181.5 | 8.480 | 117 | 62 0956 | 185.9 | 11.330 | 138 | 48 9034 | 217.0 | 11.610 | 191 |
| 10 Minutes | | 175.8 | 8.290 | 121 | | 170.7 | 8.910 | 95 | | 179.5 | 9.910 | 140 |
| Week 2 | | 162.0 | 7.680 | 100 | | 156.2 | 9.090 | 71 | | 203.1 | 12.060 | 99 |
| Week 4 | | 219.1 | 13.870 | 174 | | 179.4 | 7.600 | 101 | | 210.2 | 10.590 | 96 |
| Baseline | 50 5957 | 201.9 | 8.790 | 127 | 60 2360 | 106.4 | 3.750 | 45 | 50 6361 | 207.2 | 11.770 | 227 |
| 10 Minutes | | 182.0 | 8.200 | 152 | | 132.0 | 5.930 | 70 | | 157.1 | 7.900 | 171 |
| Week 2 | | 186.6 | 7.680 | 129 | | 137.5 | 6.650 | 60 | | 199.2 | 10.870 | 113 |
| Week 4 | | 203.7 | 8.750 | 83 | | 157.4 | 7.600 | 56 | | 187.0 | 9.770 | 200 |
| Baseline | 11 8412 | 129.9 | 5.070 | 49 | 48 5450 | 150.5 | 7.390 | 100 | 54 4374 | 179.9 | 8.650 | 157 |
| 10 Minutes | | 173.4 | 7.860 | 94 | | 136.3 | 6.770 | 108 | | 187.2 | 9.600 | 186 |
| Week 2 | | 177.3 | 7.580 | 167 | | 180.3 | 10.470 | 123 | | 170.6 | 8.780 | 154 |
| Week 4 | | 130.7 | 6.510 | 48 | | 184.2 | 10.060 | 203 | | 185.7 | 9.870 | 119 |
| Baseline | 54 2855 | 154.5 | 6.110 | 85 | 50 7599 | 212.6 | 13.050 | 199 | 60 5745 | 189.3 | 9.370 | 165 |
| 10 Minutes | | 155.3 | 7.710 | 94 | | 161.9 | 8.780 | 122 | | 178.4 | 9.370 | 141 |
| Week 2 | | 182.2 | 9.000 | 163 | | 155.4 | 8.800 | 118 | | 181.5 | 9.930 | 116 |
| Week 4 | | 139.5 | 6.380 | 106 | | 177.5 | 9.140 | 166 | | 216.0 | 11.100 | 122 |
| Baseline | 56 5116 | 181.9 | 8.750 | 117 | 66 6453 | 187.1 | 9.570 | 189 | 52 0789 | 199.0 | 9.320 | 167 |
| 10 Minutes | | 208.9 | 11.630 | 172 | | 182.6 | 10.900 | 161 | | 181.0 | 8.440 | 135 |
| Week 2 | | 198.9 | 10.060 | 152 | | 177.2 | 10.400 | 123 | | 182.6 | 8.260 | 124 |
| Week 4 | | 202.5 | 9.630 | 157 | | 180.5 | 9.870 | 165 | | 193.2 | 9.370 | 135 |
| Baseline | 44 8978 | 208.3 | 10.680 | 165 | 48 1570 | 189.5 | 10.070 | 147 | 54 4039 | 147.6 | 9.040 | 89 |
| 10 Minutes | | 160.2 | 7.690 | 136 | | 191.9 | 9.680 | 144 | | 168.8 | 8.020 | 146 |
| Week 2 | | 218.2 | 11.740 | 176 | | 196.7 | 10.510 | 170 | | 149.2 | 7.970 | 128 |
| Week 4 | | 217.8 | 10.960 | 186 | | 179.7 | 9.410 | 133 | | 124.3 | 7.220 | 84 |
| Baseline | 54 8532 | 233.8 | 11.790 | 125 | 62 3461 | 186.7 | 10.860 | 171 | 68 5881 | 151.5 | 10.080 | 113 |
| 10 Minutes | | 200.5 | 10.240 | 192 | | 146.2 | 7.760 | 112 | | 150.3 | 9.750 | 103 |
| Week 2 | | 217.0 | 12.150 | 143 | | 169.0 | 9.210 | 148 | | 186.1 | 9.770 | 167 |
| Week 4 | | 207.0 | 10.170 | 208 | | 177.0 | 10.270 | 155 | | 97.8 | 4.340 | 28 |
| Baseline | 54 7549 | 180.3 | 8.090 | 139 | 60 8470 | 173.4 | 11.810 | 211 | 50 3320 | 191.8 | 9.070 | 100 |
| 10 Minutes | | 169.4 | 8.330 | 106 | | 168.9 | 9.480 | 62 | | 163.2 | 7.870 | 74 |
| Week 2 | | 192.0 | 9.100 | 178 | | 194.1 | 13.180 | 93 | | 178.9 | 7.630 | 123 |
| Week 4 | | 215.8 | 10.760 | 166 | | 198.0 | 13.380 | 78 | | 181.8 | 7.650 | 105 |
| Baseline | 68 7601 | 200.1 | 8.970 | 112 | 64 0508 | 175.0 | 9.540 | 140 | 62 3368 | 219.0 | 8.470 | 145 |
| 10 Minutes | | 150.7 | 7.510 | 85 | | 168.6 | 8.910 | 108 | | 244.9 | 9.070 | 87 |
| Week 2 | | 180.4 | 8.130 | 99 | | 174.2 | 9.050 | 170 | | 203.7 | 7.710 | 121 |
| Week 4 | | 214.8 | 9.360 | 127 | | 155.7 | 7.770 | 126 | | 183.6 | 6.900 | 123 |
| Baseline | 66 0675 | 186.7 | 8.470 | 108 | 58 6382 | 182.4 | 10.140 | 93 | 60 7089 | 179.3 | 10.020 | 153 |
| 10 Minutes | | 177.1 | 6.720 | 92 | | 129.4 | 8.030 | 94 | | 166.3 | 10.210 | 106 |
| Week 2 | | 128.4 | 5.360 | 59 | | 180.3 | 9.830 | 152 | | 155.7 | 8.400 | 115 |
| Week 4 | | 186.1 | 7.020 | 86 | | 181.4 | 9.120 | 141 | | 132.6 | 6.170 | 117 |
| Baseline | 40 6591 | 221.6 | 11.510 | 103 | 58 7856 | 130.9 | 5.270 | 59 | 50 6134 | 180.6 | 10.940 | 150 |
| 10 Minutes | | 223.9 | 12.430 | 107 | | 136.3 | 6.470 | 87 | | 170.4 | 9.580 | 115 |
| Week 2 | | 212.9 | 9.340 | 106 | | 188.6 | 9.790 | 107 | | 166.2 | 8.730 | 170 |
| Week 4 | | 202.7 | 11.490 | 127 | | 214.2 | 9.950 | 78 | | 174.8 | 8.090 | 69 |
| Baseline | 52 8160 | 197.6 | 10.940 | 178 | | | | | | | | |

TABLE 9

Skin Replica Analysis - Statistics - Changes from Baseline; and Summary
of the Performances of the Panel Exhibiting Smoothing of Wrinkles
SKIN REPLICA IMAGE ANALYSIS - STATISTICS -
CHANGES FROM BASELINE
Test of means against reference constant (value = 0) (cfbdata)

| Parameter | N | Mean | Std. Dv. | t-value | p | Improvement % |
|---|---|---|---|---|---|---|
| 10 Minutes | | | | | | |
| Rz | 34 | −10.8 | 24.6 | −2.5625 | 0.0151 | 5.9 |
| IDL | 34 | −0.55 | 1.78 | −1.8079 | 0.0797 | 5.9 |
| NumwR | 34 | −13.4 | 43.8 | −1.7805 | 0.0842 | 9.9 |
| Week 2 | | | | | | |
| Rz | 34 | −3.2 | 25.8 | −0.7257 | 0.4731 | 1.8 |
| IDL | 34 | −0.20 | 1.99 | −0.5902 | 0.5591 | 2.1 |
| NumWr | 34 | −6.0 | 54.4 | −0.6426 | 0.5249 | 4.5 |
| Week 4 | | | | | | |
| Rz | 34 | −0.2 | 28.1 | −0.0476 | 0.9624 | 0.1 |
| IDL | 34 | −0.29 | 2.46 | −0.6849 | 0.4982 | 3.1 |
| NUMwR | 34 | −10.9 | 48.9 | −1.3019 | 0.2020 | 8.1 |

SUMMARY OF THE PERFORMANCES OF THE PANEL
EXHIBITING SMOOTHING OF WRINKLES

| Study Time Point | Rz | IDL | NumWr | MEAN: |
|---|---|---|---|---|
| 10 Minutes | 68% | 62% | 59% | 63% |
| Week 2 | 65% | 56% | 47% | 56% |
| Week 4 | 59% | 56% | 62% | 59% |

Rz—the average maximum difference in luminance value for five equal length segments in each of the 10 lines traversing the sample.
IDL—the integrated developed length of the luminance traces of the 10 scan lines. This is the total length of the luminance lines as a proportion of the straight line distance. I.E. a flat featureless sample has an IDL of 1.000.
NumWr—the total number of features detected in the 10 bands or sub-areas used to calculate spacing and breadth.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above, including U.S. provisional application 61/524,021, filed Aug. 16, 2011, are hereby incorporated in their entirety by reference.

We claim:

1. A system for treating damaged skin, comprising a cosmeceutical formulation which comprises:
   about 1-10% of a mixture of perfluorocarbons (PFC's) of at least three different molecular weights,
   about 0.001-5% hyaluronic acid (HA) of molecular weight about 100 kDa or less,
   about 0.1-20% of emulsifier(s);
   packaged in an aerosol spray hand-held container.

2. The system of claim 1, wherein the cosmeceutical formulation is aqueous.

3. The system of claim 1, wherein the cosmeceutical formulation comprises an oil and water emulsion.

4. The system of claim 1, wherein the mixture of PFC's comprises perfluoropropane, perfluorobutane, perfluoropentane, perfluorohexane, perfluorodecalin, perfluorodimethylcyclohexane, perfluoroperhydrophenanthrene, pentafluoropropane, perfluorotripropylamine, $C_6$-$C_9$ perfluoroalkanes, perfluoroperhydrofluoranthrene, perfluorodecalin, perfluoroperhydro-phenanthrene, bis(perfluor-hexyl)-1,2-ethene, perfluoro-1,3-dimethylcyclohexane, perfluoro-methyldecalin, perfluoroisopropyldecalin, a mixture of perfluorodixylylmethane and perfluorodixylylethane, and/or a mixture of perfluoroperhydrophenanthrene and perfluoro n-butyl decalin.

5. A method for treating damaged skin, comprising administering with an aerosol spray hand-held container a cosmeceutical formulation comprising
   about 1-10% of a mixture of perfluorocarbons of at least three different molecular weights,
   about 0.001-5.0% hyaluronic acid of molecular weight about 100 kDa or less, and
   about 0.1-20% of emulsifier(s).

6. The method of claim 5, wherein the cosmeceutical formulation comprises an oil and water emulsion.

7. The method of claim 5, wherein the cosmeceutical formulation comprises about 10% perfluorocarbons.

8. The method of claim 5, which is effective for aiding in wound healing, treating sunburn or acne lesions, treating damage resulting from chemical peels, increasing skin moisturization, and/or reducing fine lines and wrinkles.

9. The system of claim 1, wherein the cosmeceutical formulation further comprises one or more of niacin or other vitamins, minerals, enzymes, amino acids, antioxidants, blood dilating ingredients, or a fragrance.

10. The system of claim 1, wherein the cosmeceutical formulation further comprises HSC (Hydrophobic Sphingolipid Complex), Atoxelene; and a fragrance.

11. The system of claim 1, wherein the cosmeceutical formulation further comprises: an intracellular oxygen booster (0.005-30%); emulsifiers, (0.1-20%); rheology modifiers, (0.05-5%); humectants (0.5-8%); surfactants (0.1-5%); and emollients (0.1-20%); and optionally further comprises one or more of pH modifiers (0.005-2%); antimicrobial agents (0.001-3%); colorants (0.001-30%); aromas (0.005-5%); or antioxidants (0.005-5%).

12. The system of claim 11, wherein the intracellular oxygen booster is Tropaeolum Majus Flower/Leaf/Stem Extract; the emulsifier is a nonionic, cationic, anionic or polymeric emulsifier; the rheology modifier is a polyacrylic acid polymer, xanthan gum, cellulose gum, silicate, alginate, or hydrocolloid; the humectant is propanediol, glycerin or another glycol; the surfactant is cationic, anionic, ethoxylated or non-ethoxylated; the antimicrobial agent is salicylic acid or a preservative; the colorant is an FD&C color, iron oxide, or titanium dioxide; the aroma is in the form of a fragrance or essential oil; and the antioxidant is ascorbic acid.

13. The system of claim 1, wherein the formulation is for treatment of adult acne, and the formulation further comprises salicylic acid.

14. The system of claim 1, wherein the formulation is for treatment of cellulite, and the formulation further comprises adipogenesis inhibitors, lipogenesis inhibitors, and/or or lipolytic agents.

15. The system of claim 1, wherein the formulation is for use as a foundation for make-up, and the formulation further comprises one or more suitable colorants.

16. The system of claim 1, wherein the molecular weight of the HA is less than or about 50 kDa.

17. The system of claim 1, wherein the HA is in an amount of about 0.1%.

18. The system of claim 1, wherein the formulation is partially saturated, saturated, or supersaturated with oxygen.

19. An aerosol container comprising, under pressure, a cosmeceutical formulation comprising
   about 1-10% of a mixture of perfluorocarbons (PFC's) of at least three different molecular weights, about 0.001-5% hyaluronic acid (HA) of molecular weight about 100 kDa or less, and about 0.1-20% of emulsifier(s).

20. The aerosol container of claim 19, wherein the cosmeceutical formulation comprises an oil and water emulsion.

21. The system of claim 1, wherein the cosmeceutical formulation, when administered with the aerosol spray hand-held container, forms a foam.

22. The system of claim 1, wherein the cosmeceutical formulation further comprises about 0.005-30% Tropaeolum Majus Flower/Leaf/Stem Extract.

23. The system of claim 1, wherein the cosmeceutical formulation is partially saturated with oxygen.

24. A system for treating damaged skin, comprising a cosmeceutical formulation which comprises:
 about 1-10% of a mixture of perfluorocarbons (PFC's) of at least three different molecular weights,
 about 0.001-5% hyaluronic acid (HA) of molecular weight about 100 kDa or less, and
 about 0.1-5% of surfactant(s);
 packaged in an aerosol spray hand-held container.

25. A system for treating damaged skin, comprising a cosmeceutical formulation which comprises:
 about 1-10% of a mixture of perfluorocarbons (PFC's) of at least three different molecular weights,
 about 0.001-5% hyaluronic acid (HA) of molecular weight about 100 kDa or less, and
 an intracellular oxygen booster (0.005-30%);
 packaged in an aerosol spray hand-held container.

* * * * *